United States Patent
Goel

(10) Patent No.: US 9,815,777 B2
(45) Date of Patent: Nov. 14, 2017

(54) METFORMIN SALTS TO TREAT TYPE2 DIABETES

(71) Applicant: Jiva Pharma, Inc., Ann Arbor, MI (US)

(72) Inventor: Om P Goel, Ann Arbor, MI (US)

(73) Assignee: Jiva Pharma, Inc., Ann Arbor, MI (US)

( * ) Notice: Subject to any disclaimer, the term of this patent is extended or adjusted under 35 U.S.C. 154(b) by 12 days.

(21) Appl. No.: 15/022,951

(22) PCT Filed: Sep. 20, 2014

(86) PCT No.: PCT/US2014/056700
§ 371 (c)(1),
(2) Date: Mar. 18, 2016

(87) PCT Pub. No.: WO2015/042495
PCT Pub. Date: Mar. 26, 2015

(65) Prior Publication Data
US 2016/0229796 A1    Aug. 11, 2016

Related U.S. Application Data

(60) Provisional application No. 61/880,948, filed on Sep. 22, 2013.

(51) Int. Cl.
| | | |
|---|---|---|
| C07C 277/00 | (2006.01) | |
| C07C 281/00 | (2006.01) | |
| C07D 277/00 | (2006.01) | |
| C07C 279/26 | (2006.01) | |
| A61K 31/4439 | (2006.01) | |
| C07D 417/12 | (2006.01) | |
| A61K 31/155 | (2006.01) | |
| C07D 277/34 | (2006.01) | |

(52) U.S. Cl.
CPC ........ *C07C 279/265* (2013.01); *A61K 31/155* (2013.01); *A61K 31/4439* (2013.01); *C07D 277/34* (2013.01); *C07D 417/12* (2013.01)

(58) Field of Classification Search
CPC .... C07C 277/00; C07C 281/00; C07D 277/00
USPC ................................ 564/227, 241; 548/146
See application file for complete search history.

(56) References Cited

U.S. PATENT DOCUMENTS

| | | |
|---|---|---|
| 4,687,777 A | 8/1987 | Meguro et al. |
| 6,031,004 A | 2/2000 | Timmins et al. |
| 6,437,143 B2 | 8/2002 | Moinet et al. |
| 2008/0031964 A1 | 2/2008 | Messadek |
| 2011/0171142 A1 | 7/2011 | Lara |

FOREIGN PATENT DOCUMENTS

| | | | | |
|---|---|---|---|---|
| WO | WO 2007009799 A1 * | 1/2007 | ........... | C07D 417/12 |
| WO | WO 2012090225 A2 * | 7/2012 | ........... | A61K 31/155 |
| WO | WO 2012148252 A2 * | 11/2012 | ........... | C07C 279/26 |

OTHER PUBLICATIONS

Avandamet Prescribing Information (published 2007).*

* cited by examiner

*Primary Examiner* — Timothy Thomas
*Assistant Examiner* — George W Kosturko
(74) *Attorney, Agent, or Firm* — Technology Law PLLC; Karen L Kimble

(57) ABSTRACT

Metformin salts of 2,4-thiazolidinediones are described for the treatment of diabetes mellitus Type2, gestational diabetes, polycystic ovary syndrome, non-alcoholic fatty liver disease, coronary artery disease, pancreatic cancer, premature puberty, and other diseases which manifest insulin resistance.

7 Claims, 8 Drawing Sheets

METFORMIN SALTS TO TREAT TYPE2 DIABETES

BACKGROUND OF THE INVENTION

Field of the Invention

Metformin 2,4-dioxothiazolidin-3-ide(s), metformin salts of 2,4-thiazolidinedione, or metformin salts of rosiglitazone or pioglitazone are described for the treatment of diabetes mellitus Type2, gestational diabetes, coronary artery disease, polycystic ovary syndrome, premature puberty, non-alcoholic fatty liver disease, cancer such as pancreatic cancer, and other diseases which manifest insulin resistance.

Also, included are the prodrugs (N—((N—(N,N-dimethylcarbamimidoyl)carbamimidoyl)carbamoyl)-2-mercaptoacetamide) and N—((N—(N,N-dimethylcarbamimidoyl)carbamimidoyl)carbamoyl)-2-mercaptoacetamide•metformin.

Description of Related Art

Metformin as its hydrochloride salt is widely prescribed and is the drug of choice for the treatment of diabetes mellitus Type2 (T2D), characterized by insulin resistance, especially in overweight patients. Insulin resistance is the inability of the pancreas to produce sufficient insulin and/or muscle, fat, and liver cells to utilize available insulin for the uptake of glucose. Metformin is the only antidiabetic drug that has been conclusively shown to prevent the cardiovascular complications of diabetes. It helps reduce LDL cholesterol and triglyceride levels, and is not associated with weight gain. As of 2010, metformin is one of only two oral antidiabetics in the World Health Organization Model List of Essential Medicines (the other being glibenclamide) (Wikipedia).

Additionally, metformin is increasingly being used in polycystic ovary syndrome (PCOS), non-alcoholic fatty liver disease (NAFLD) and premature puberty; three other diseases that feature insulin resistance (Wikipedia).

Most common adverse effects of metformin hydrochloride is gastrointestinal upset, including diarrhea, cramps, nausea, vomiting and increased flatulence; possibly due to the high dose of 1-2.5 g/daily, and is usually managed by a starting low dose and building up to the maintenance dose, or through extended release formulations.

Organic acid salts of metformin have been prepared. For example U.S. Pat. No. 6,031,004 describes metformin salts of dibasic acids (2:1 molar ratio), metformin (2:1) fumarate, and metformin (2:1) succinate. Published EP 2303838A1 describes the 1:1 glycinate salt of metformin Published WO 2011025271A describes the preparation and formulations of metformin ascorbate. None of these products have yet reached the market.

2,4-Thiazolidinedione is an integral, covalently linked, structural moiety in a class of highly successful potent Type2 diabetes drugs known as the thiazolidinediones (TZDs). These TZDs act by activating PPARs (peroxisome proliferator-activated receptors), a group of nuclear receptors, with greatest specificity for PPARγ (gamma). The endogenous ligands for these receptors are free fatty acids (FFAs) and eicosanoids. When activated, the receptor binds to DNA in complex with the retinoid X receptor (RXR), another nuclear receptor, increasing transcription of a number of specific genes and decreasing transcription of others. Through a series of steps this leads to a decrease in insulin resistance, and improved lipid profile (Wikipedia). The best known therapeutic agents in the TZDs class are: rosiglitazone, (RS)-5-[4-(2-[methyl(pyridin-2-yl)amino]ethoxy)benzyl]thiazolidine-2,4-dione maleate (Avandia®, trademark of SmithKline Beecham), and pioglitazone, (RS)-5-(4-[2-(5-ethylpyridin-2-yl)ethoxy]benzyl)thiazolidine-2,4-dione hydrochloride (Actos®, trademark of Takeda Pharmaceutical Company). These are highly effective, low dose, insulin sensitizers that were approved by the FDA and market launched in the 1990s for treating T2D. Surprisingly, there appear to be no known mechanistic studies of the 2,4-thiazolidinedione moiety when used alone as a hypoglycemic agent, or its activity as a ligand binding at the PPARs (peroxisome proliferator-activated receptors).

The TZDs are generally prescribed in conjunction with metformin hydrochloride, either separately, or as an admixture in one pill. For example, Avandamet® is a combination therapy of rosiglitazone maleate and metformin hydrochloride (2-4 mg plus 500 mg, respectively; once or twice daily). Similarly, ActoPlus Met is a combination pill of pioglitazone hydrochloride and metformin hydrochloride (15 mg plus 500-850 mg, respectively; once or twice daily). A disadvantage of this therapy is that the adverse effects of metformin hydrochloride as gastrointestinal upset are still present.

Saxagliptin (Onglyza®, trademark of Astrazeneca AB), Sitagliptin (Januvia®, trademark of Merck & Co), and Alogliptin (Nesina®, trademark of Takeda Pharmaceutical Company Ltd) are antidiabetic drugs in a new class of dipeptidyl peptidase-4 (DPP-4) inhibitors. These are prescribed alone or in a combination with metformin hydrochloride, e.g., as Janumet®, trademark of Merck & Co. Other DPP-4 inhibitors are nearing FDA approval. Recently reported large clinical studies suggest that the gliptins, while they did not increase heart attack risk compared with a placebo, did not lower that risk. There was significantly more risk of heart failure and hospitalizations with one of the drugs (Wall Street Journal Sep. 3, 2013 B3). The clinical expert opinion is that lowering glucose level should be accompanied with improved cardiovascular health, such as by lowering of cholesterol and blood pressure.

Clearly, finding a drug that treats insulin resistant diseases, while having the needed safety for cardiovascular and gastrointestinal concerns, is still needed.

BRIEF SUMMARY OF THE INVENTION

The present invention provides compounds of the formula

Formula (A)

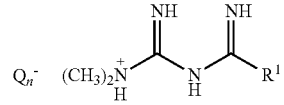

wherein:
when n is 1, then $R^1$ is —$NH_2$, or

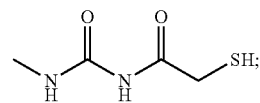

and Q is $Cl^-$,

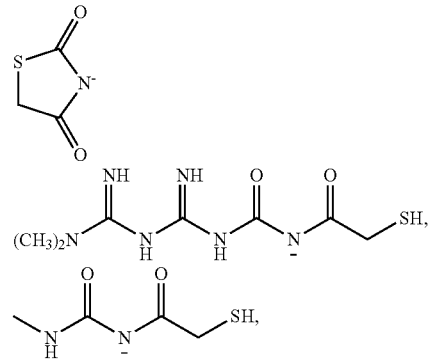

-continued

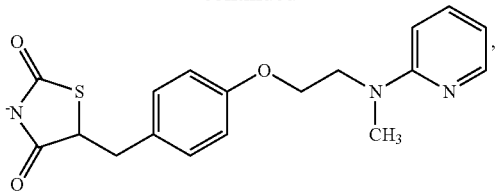

or

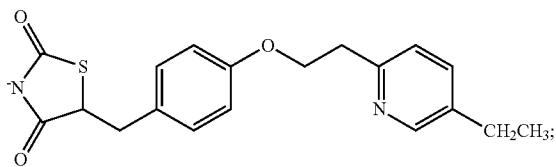

and provided that when $R^1$ is —$NH_2$, Q is other than $Cl^-$; and when n is 0, then $R^1$ is

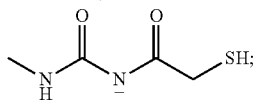

and with the proviso that a neutral compound of Formula (A) is obtained.

Formulae (I)-(VII) below can be expressed as one Formula (A) as shown above. As ionic compounds are formed, the overall charge is neutral. Thus the anion portion, Q, is provided by the salt, another entity or within the same structure. Preferred compounds of Formula (A) are those wherein: n is 1; $R^1$ is —$NH_2$; and Q is

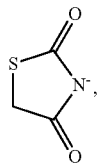

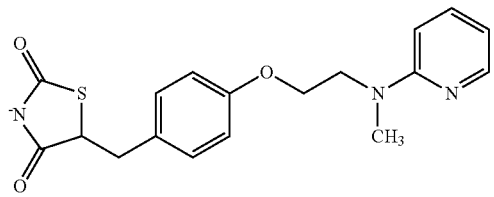

or

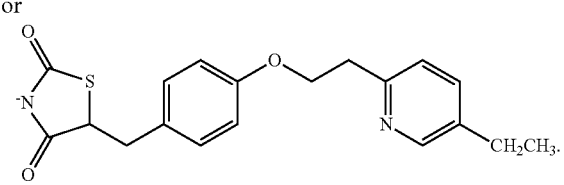

These compounds are formulated using customary pharmaceutically-acceptable diluents, excipients, buffers, and preseratives and are administered as tablets (coated or uncoated), capsules, liquid gel capsules, suspensions, emulsions, injections (e.g., intramuscular, intravenous, intraperitoneal, subcutaneous), or transdermal formulations (e.g., patches or application to the skin surface, suppository compositions).

These compounds are used for the treatment of diabetes mellitus Type2, gestational diabetes, coronary artery disease, polycystic ovary syndrome, premature puberty, non-alcoholic fatty liver disease, cancer such as pancreatic cancer, and other diseases which manifest insulin resistance.

BRIEF DESCRIPTION OF THE DRAWINGS

FIG. 1 illustrates the molecular structure of MET.TZ showing the atom-labeling scheme disorder of the methyl and thiazolidine fragments. Displacement ellipsoids are drawn at the 50% probability level.

FIG. 2 illustrates the molecular structure of MET.TZ showing the atom-labeling scheme. Disorder components removed for clarity. Displacement ellipsoids are drawn at the 50% probability level.

FIG. 3 illustrates the crystal structure of MET.TZ projected down the b-axis showing the extensive network of N—H . . . O/N hydrogen bonds.

FIG. 4 illustrates the molecular structure of pioglitazone metforminate showing the atom-labeling scheme, molecular disorder, and thiazolidine fragments. Displacement ellipsoids are drawn at the 50% probability level.

FIG. 5 illustrates the molecular structure of pioglitazone metforminate, showing the atom-labeling scheme. Disorder components removed for clarity. Displacement ellipsoids are drawn at the 50% probability level.

FIG. 6 illustrates the crystal structure of pioglitazone metforminate projected down the a-axis showing the extensive network of N—H . . . O/N hydrogen bonds.

DETAILED DESCRIPTION OF THE INVENTION

Figure 1:
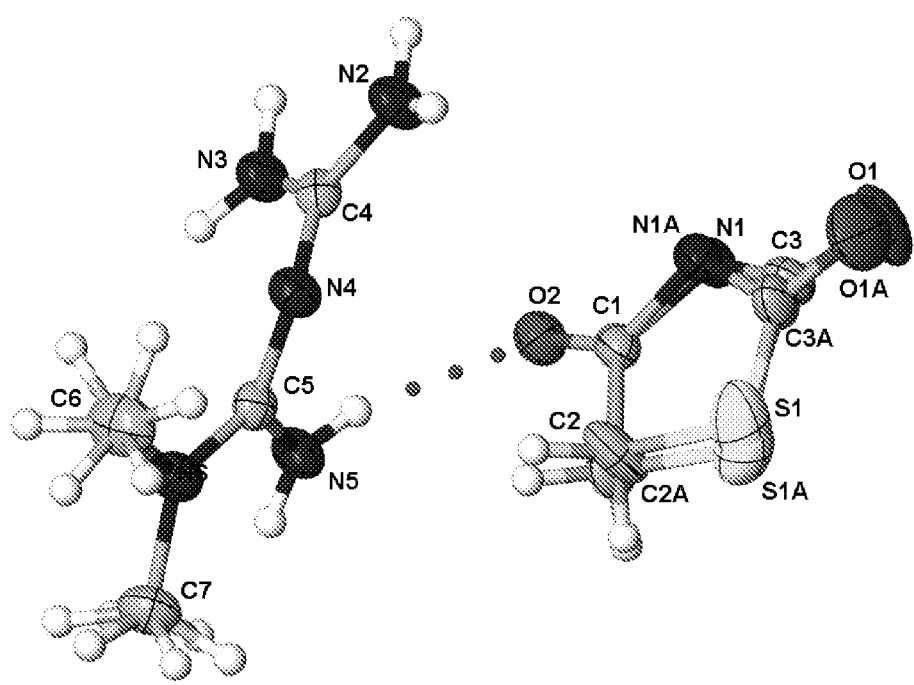
In FIGS. 1-6 the various colors are: yellow is sulfur; gray is carbon; white is hydrogen; blue is nitrogen; and red is oxygen.

It is understood that the terminology used herein is for the purpose of describing particular embodiments only and is not intended to be limiting. As used in this specification, the singular forms "a", "an", and "the" include plural referents unless the content clearly indicates otherwise.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent is not included for this application.

GLOSSARY

DMG means dimethylglyoxime
DPP-4 inhibitors means dipeptidyl peptidase-4 inhibitors FFAs means free fatty acids
Met-TZ or Met.TZ means 1:1 metformin salt of 2,4-thiazolidinedione
NAFLD means non-alcoholic fatty liver disease
Overnight means from about 8 hours to about 16 hours
PCOS means polycystic ovary syndrome
Pioglitazone means (RS)-5-(4-[2-(5-ethylpyridin-2-yl)ethoxy]benzyl)thiazolidine-2,4-dione hydrochloride
PPARs means peroxisome proliferator-activated receptors
Rosiglitazone means (RS)-5-[4-(2-[methyl(pyridin-2-yl)amino]ethoxy)benzyl]thiazolidine-2,4-dione maleate
RT means room temperature or ambient temperature or about 22 to about 25° C.
T2D means diabetes mellitus Type2
TZDs means thiazolidinediones from the class of compounds known as PPARγ agonists which are in clinical use to treat Type2 diabetes and exemplified by pioglitazone hydrochloride and rosiglitazone maleate Metformin belongs in the bisguanide class of antidiabetic drugs and occurs naturally in the French lilac or goat's rue (*Galega officinalis*), a plant used in folk medicine for several centuries (Wikipedia). Metformin as its hydrochloride salt is sold under several trade names, including Glucophage XR® (trademark of Merck-Sante), Carbophage SR, Riomet® (trademark of Ranbaxy Laboratories Ltd), Fortamet® (trademark of Shionogi Inc.), Glumetza® (trademark of Valeant International), Obimet, Gluformin, Dianben, Diabex, Diaformin, Siofor, and Metfogamma Metformin IR (immediate release) is available in 500 mg, 850 mg, and 1000 mg tablets.

The metformin salts (1:1 and 1:2) of 2,4-thiazolidinedione itself, have not been reported or studied in the treatment of Type2 diabetes. These salts are expected to have an advantage of better gastrointestinal tolerance and a better therapeutic index than metformin hydrochloride due to the acid neutralizing or buffering ability of the amphoteric 2,4-thiazolidinedione moiety. Also, there is no reported study of the hypoglycemic activity of the 2,4-thiazolidinedione moiety itself.

In one study conducted for this invention in db/db mice, 2,4-thiazolidinedione with metformin as its salt (1:1), enhanced the glucose lowering effect of metformin, as well as glucose tolerance, post study. Thus, there is a synergistic hypoglycemic activity found with the salt (1:1) in one animal model of Type2 diabetes. Even a modest hypoglycemic effect of 2,4-thiazolidinedione in animal models of Type2 diabetes would be amplified at the required 1-1.5 g/day therapeutic doses of metformin. The hypoglycemic activity of 2,4-thiazolidinedione, without any metformin, was also examined in the same model and had little effect on glucose lowering. It should be noted that the proposed salts and prodrugs of the present invention are novel chemical entities made up of definite stoichiometric proportions, and are not physical admixtures.

2,4-Thiazolidinedione Salts of Metformin

To mitigate the gastrointestinal side effects of metformin hydrochloride, 2,4-thiazolidinedione salts of metformin are provided by this invention as Formula (I). 2,4-Thiazolidinedione is commercially available in 90-98% purity, is a weak acid, but sufficiently acidic to form amine salts. For example, the ammonium and a few primary amine salts are reported [see Popov-Pergal et al., *J. of Serbian Chem. Soc.* 1986, 51 (9-10), 507-9, and earlier references therein]. 2,4-Thiazolidinedione also has buffering capability in the strongly acidic stomach environment. As part of the present investigation, a metformin salt of 2,4-thiazolidinedione in the stoichiometric ratio of 1:1 (Met.TZ) was tested in db/db mouse model of diabetes, and found to lower glucose more than the equivalent dose of metformin hydrochloride alone. Therefore, Met.TZ is anticipated and believed to be an antidiabetic agent with a potentially better GI safety profile than metformin hydrochloride, and have an improved overall therapeutic index over metformin hydrochloride as a hypoglycemic agent.

Prodrugs

This invention considers various compounds of metformin as prodrugs as discussed in this section. In one aspect a covalent prodrug of metformin and 2,4-thiazolidinedione is a 1:1 adduct which in the body would deliver metformin and 2,4-thiazolidinedione with possible improved pharmacokinetics and improved therapeutic properties. Also, while not wishing to be bound by theory, another prodrug is a 2:1 adduct and considered a part of this invention (Formula II). These prodrugs may be made by nucleophilic addition of a metformin nitrogen at the carbonyl group adjacent to the sulfur in the 2,4-thiazolidinedione that in turn prepares N—((N—(N,N-dimethylcarbamimidoyl)carbamimidoyl)carbamoyl)-2-mercaptoacetamide. This prodrug may be stable as such or as its hydrochloride salt.

Another prodrug, N—((N—(N,N-dimethylcarbamimidoyl)carbamimidoyl)carbamoyl)-2-mercaptoacetamide•metformin is anticipated by reaction of 2 equivalents of metformin and 1 equivalent of 2,4-thiazolidinedione (Formula III).

However, during attempts to synthesize the above prodrugs, none could be isolated, even at high reaction temperature or under strongly acidic conditions of condensing metformin with 2,4-thiazolidinedione. Apparently, the 2,4-thiazolidinedione is highly stable and does not lend itself to nucleophilic additive ring opening by metformin under even stringent reaction conditions. Other routes to prepare them are being envisioned and deemed possible.

Metformin with TZDs

Another aspect of the present invention is that the 2,4-thiazolidinedione is an integral, covalently linked moiety, in a class of highly successful Type2 diabetes drugs known as TZDs. Rosiglitazone, (RS)-5-[4-(2-[methyl(pyridin-2-yl)amino]ethoxy)benzyl]thiazolidine-2,4-dione maleate (Avandia®, trademark of SmithKline Beecham), and pioglitazone, (RS)-5-(4-[2-(5-ethylpyridin-2-yl)ethoxy]benzyl)thiazolidine-2,4-dione hydrochloride (Actos®, trademark of Takeda Pharmaceutical Company) are highly effective insulin sensitizers that were approved by the FDA and market launched in the 1990s for treating Type2 diabetes. These products are generally prescribed in conjunction with metformin hydrochloride, either separately, or as an admixture in one pill. Another purpose of the present invention is to synthesize novel 1:1 salts of rosiglitazone and pioglitazone with metformin, Formula VI and Formula VII. These may be clinically used, if needed, in conjunction with the 1:1 metformin:2,4-thiazolidinedione salt, leading to better GI tolerance, and improved therapeutic index.

As expected for salts, they can exist in equilibrium ionic forms in an aqueous solvent as shown by the various formulae below. These compounds are believed new together with their pharmaceutical formulations for the utilities taught.

Metformin Salts

This invention provides a pharmaceutically-acceptable formulation comprising metformin salts of the formulae below in the molecular stoichiometric ratio of 1:1 as novel compounds for the treatment of Type 2 diabetes, cardiovascular disease, polycystic ovary syndrome, non-alcoholic fatty liver disease, cancer such as pancreatic cancer, and other diseases which manifest insulin resistance. A single crystal x-ray structure of the 1:1 salt was obtained and is reported below, Formula (I).

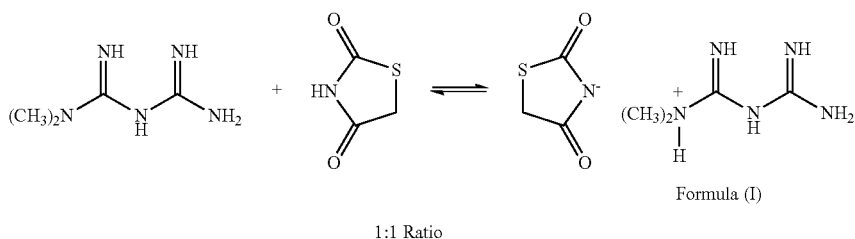

Formula (I)

1:1 Ratio

This 1:1 Ratio of Formula (I) was obtained and further characterized below.

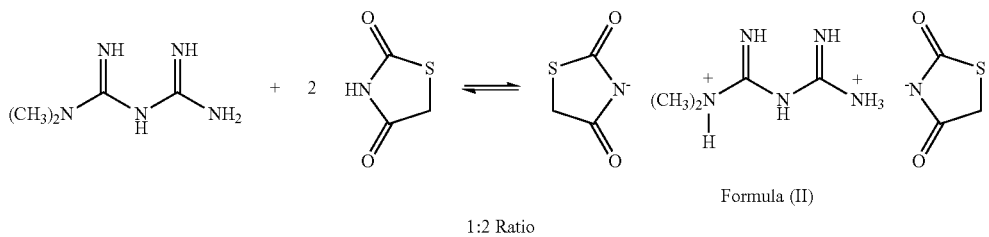

Formula (II)

1:2 Ratio

Another aspect of the invention is to provide the 1:1 adduct prodrug of metformin and 2,4-thiazolidinedione, N—((N—(N,N-dimethylcarbamimidoyl)carbamimidoyl)-carbamoyl)-2-mercaptoacetamide (Formula (III) or Formula (IV). These adducts are anticipated to be useful for hypoglycemic activity. However, as noted earlier, these kind of adducts could not be isolated from reaction mixtures even under stringent conditions of high temperatures, polar solvents such as dimethyl sulfoxide, and strong acids, which mainly led to decompositions. These compounds are envisioned as shown below.

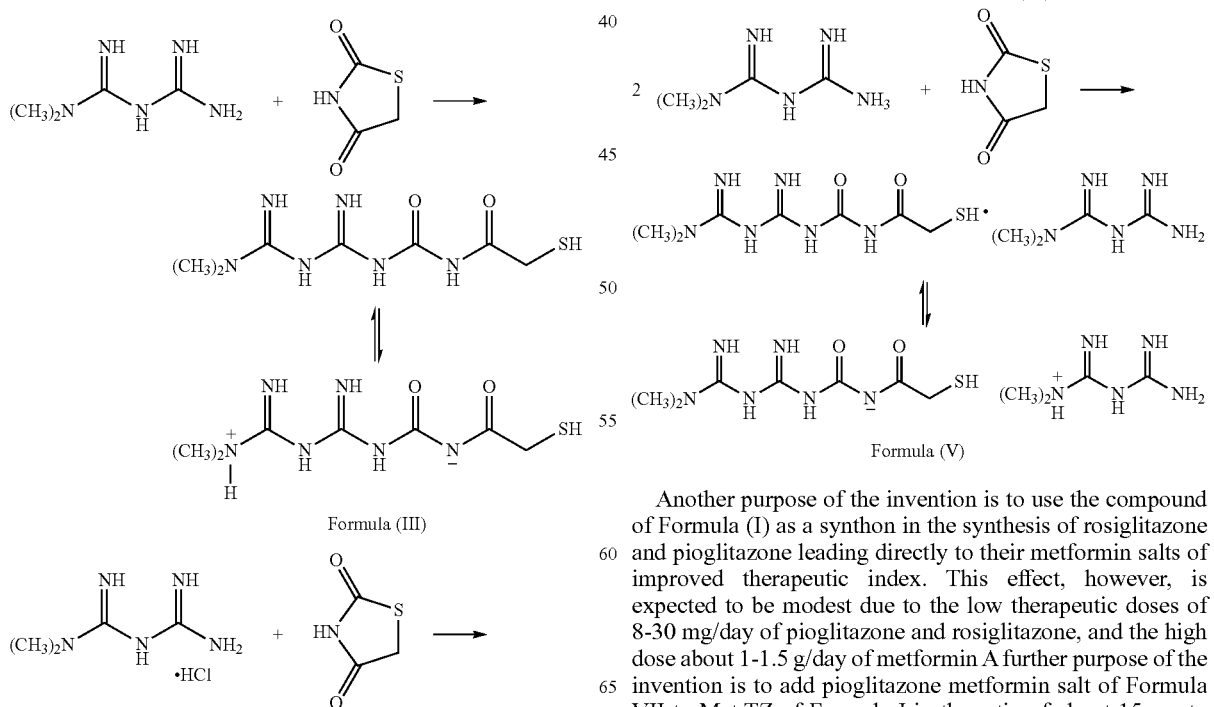

Formula (III)

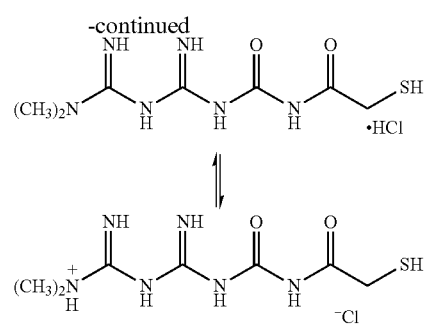

Formula (IV)

Formula (V)

Another purpose of the invention is to use the compound of Formula (I) as a synthon in the synthesis of rosiglitazone and pioglitazone leading directly to their metformin salts of improved therapeutic index. This effect, however, is expected to be modest due to the low therapeutic doses of 8-30 mg/day of pioglitazone and rosiglitazone, and the high dose about 1-1.5 g/day of metformin A further purpose of the invention is to add pioglitazone metformin salt of Formula VII to Met.TZ of Formula I in the ratio of about 15 mg to about 500 mg, respectively, or rosiglitazone metformin salt of Formula VI to Met.TZ of Formula I in the ratio of about 2 mg to about 500 mg, respectively.

These salts can be named as follows with their structures provided below:

Rosiglitazone Metforminate
(RS)-5-[4-(2-[methyl(pyridin-2-yl)amino]ethoxy)benzyl]thiazolidine-2,4-dione•metformin, (Formula VI) or when named as its salt
metformin (RS)-5-[4-(2-[methyl(pyridin-2-yl)amino]ethoxy)benzyl]thiazolidine-2,4-dioxothiazolidin-3-ide.

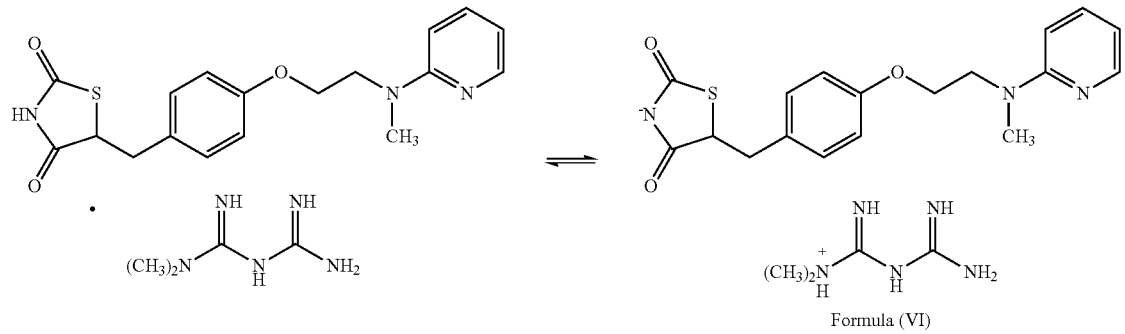

Pioglitazone Metforminate
(RS)-5-(4-[2-(5-ethylpyridin-2-yl)ethoxy]benzyl)thiazolidine-2,4-dione•metformin, (Formula VII) or when named as its salt
metformin (RS)-5-(4-[2-(5-ethylpyridin-2-yl)ethoxy]benzyl)thiazolidine-2,4-dioxothiazolidin-3-ide.

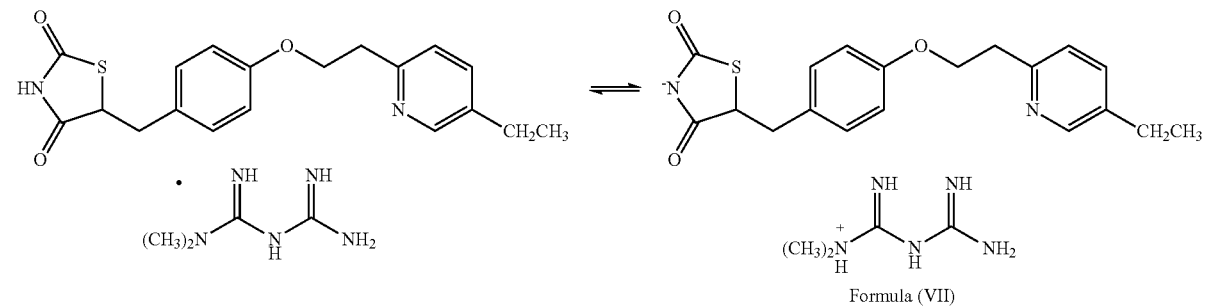

These Formulae (I)-(VII) as well as the subgroup of compounds of Formulae (I), (VI) and (VII) can be expressed as one Formula (A) as shown herein above. As ionic compounds are formed, the overall charge is neutral. Thus the anion portion is provided by the salt, another entity or within the same structure. Compounds of Formula (A) encompassing preferred Formulae (I), (VI) and (VII) are shown by Formula (A) wherein: n is 1; $R^1$ is —$NH_2$; and Q is

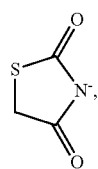

or

-continued

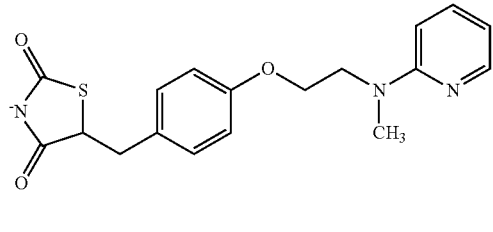

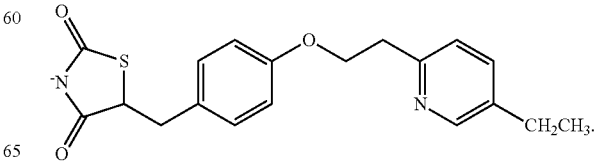

Formulations

The formulations containing compounds of Formula (A), (I), (VI), and (VII) may be administered as a tablet (coated or uncoated), capsule, liquid gel capsules, gelatin capsule, oral use syrup, suspension, emulsion, solution for injection (e.g., intramuscular, intravenous, intraperitoneal, or subcutaneous), transdermal formulations (e.g., patches or application to the skin surface, suppository compositions). One or more of customary pharmaceutically-acceptable adjuvants, binders, desiccants, diluents, excipients, buffers, and/or preseratives are present.

Utility

Metformin 2,4-dioxothiazolidin-3-ide or 1:1 metformin salt of 2,4-thiazolidinedione and their potential prodrugs (N—((N—(N,N-dimethylcarbamimidoyl)carbamimidoyl) carbamoyl)-2-mercaptoacetamide) and N—((N—(N,N-dimethylcarbamimidoyl)carbamimidoyl)carbamoyl)-2-mercaptoacetamide•metformin are used for the treatment of diabetes mellitus Type2, gestational diabetes, coronary artery disease, polycystic ovary syndrome, premature puberty, non-alcoholic fatty liver disease, cancer such as pancreatic cancer, and other diseases which manifest insulin resistance.

Also these formulations of Formula (I), (VI) and (VII), can be used in improving the effectiveness of other drugs and in treatment of hypertriglyceridemia, hypercholestolemia, diabetes, polycystic ovary syndrome, non-alcoholic fatty liver disease, premature puberty, cancer such as pancreatic cancer, and other diseases which manifest insulin resistance.

This invention will be further clarified by a consideration of the following example of synthesis of compounds of Formula (I), (VI) and (VII) which are intended to be purely exemplary of the present invention.

Example 1

Synthesis of A Compound of Formula (I)

Metformin thiazolidine-2,4-dione-3-ide or Thiazolidine-2,4-dione.metforminate of the structure

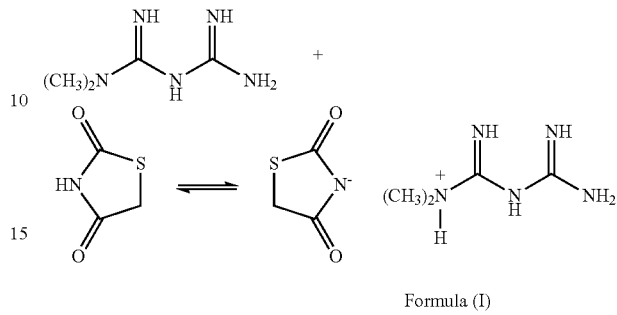

Formula (I)

A mixture of metformin free base (5.0 g, 38.6 mmol) and thiazolidine-2,4-dione (4.54 g, 38.6 mmol) were dissolved in 10 mL of hot ethanol/water solution (6 mL water, 4 mL ethanol). The solution slowly cooled to RT and stored in a −10° C. freezer overnight.

After filtration and drying, the procedure generated the mono metformin thiazolidine-2,4-dione salt (7.1 g, 75% yield) as a white solid, which is characterized by:

Melting Point: 173-175° C.;

Chromatographic purity (HPLC): 99.7% (UV; area/area; λ=220 nm);

CHN analysis: Calculated for $C_7H_{14}N_6O_2S$: 34.14; C, 5.73; H, 34.12; N. found: 34.04; C, 5.68; H, 34.30; N.

$^1$H NMR (300 MHz, DMSO-$d_6$): δ 7.13 (br s, 2H), 6.80 (br s, 4H), 3.62 (s, 2H), 2.91 (s, 6H); and $^{13}$C NMR (75 MHz, CDCl$_3$): δ 189.1, 183.1, 159.1, 158.3, 40.8, 37.5

Single crystal x-ray structure of metformin thiazolidine-2,4-dione-3-ide or thiazolidine-2,4-dione.metforminate, Formula(I) was obtained as follows:

A clear colorless block-like specimen of $C_7H_{14}N_6O_2S$, approximate dimensions 0.080 mm×0.173 mm×0.403 mm, was used for the X-ray crystallographic analysis. The X-ray intensity data were measured.

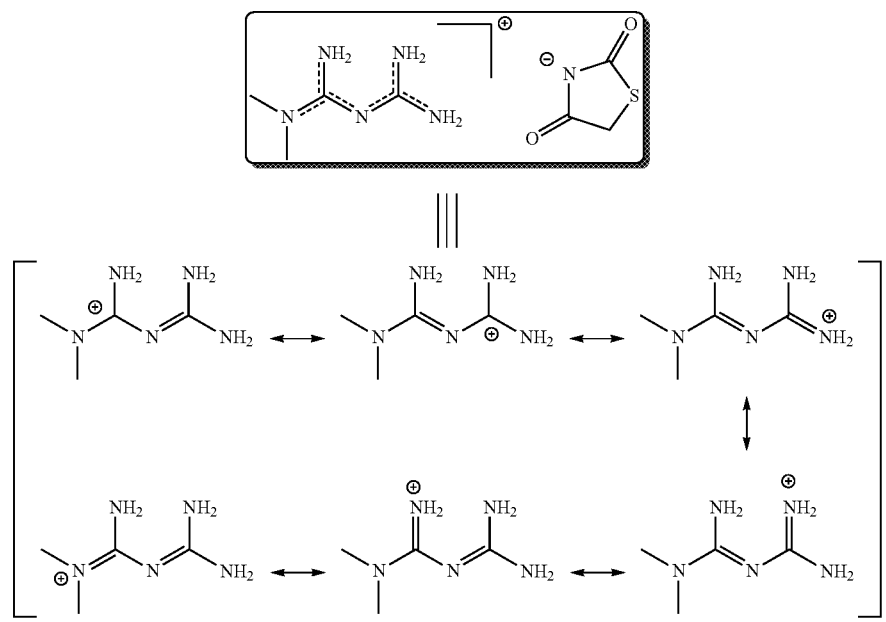

TABLE 1

| Sample and crystal data for MET.TZ. | |
|---|---|
| Identification code | MET.TZ (1:1) |
| Chemical formula | $C_7H_{14}N_6O_2S$ |
| Formula weight | 246.30 |
| Temperature | 100(2) K |
| Wavelength | 1.54178 Å |
| Crystal size | 0.080 × 0.173 × 0.403 mm |
| Crystal habit | clear colorless block |
| Crystal system | monoclinic |
| Space group | C 1 2/c 1 |
| Unit cell dimensions | a = 15.0457(3) Å  α = 90° |
|  | b = 10.7554(2) Å  β = 96.005(1)° |
|  | c = 14.5070(3) Å  γ = 90° |
| Volume | 2334.68(8) Å$^3$ |
| Z | 8 |
| Density (calculated) | 1.401 g/cm$^3$ |
| Absorption coefficient | 2.486 mm$^{-1}$ |
| F(000) | 1040 |

The molecular structure of MET.TZ showing the atom-labeling scheme disorder of the methyl and thiazolidine fragments is shown in FIG. 1. Displacement ellipsoids are drawn at the 50% probability level.

Figure 2:
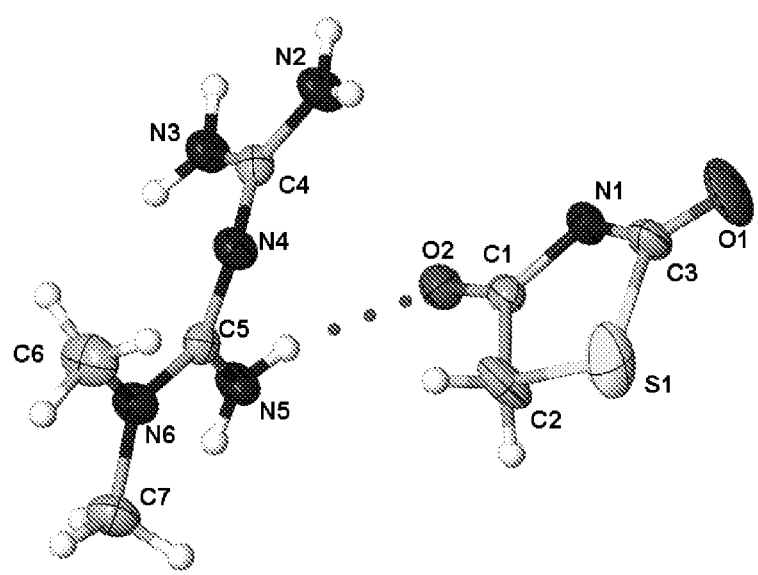

The molecular structure of MET.TZ showing the atom-labeling scheme is shown in FIG. 2. Disorder components removed for clarity. Displacement ellipsoids are drawn at the 50% probability level.

Figure 3:
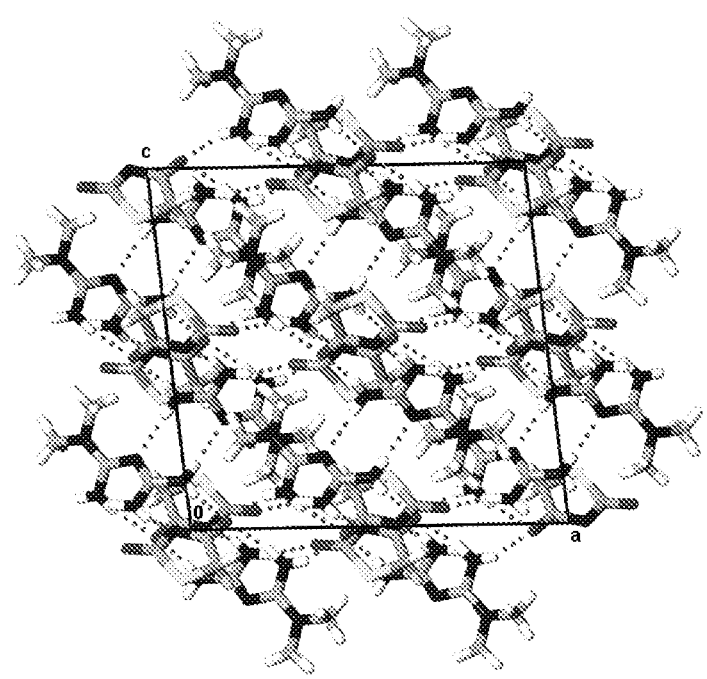

The crystal structure of MET.TZ when projected down the b-axis showing the extensive network of N—H . . . O/N hydrogen bonds is shown in FIG. 3.

Examples 2 and 3

Synthesis of a compound of Formula (VI) and (VII)

The compounds of Formulae (V) and (VI) are synthesized from the precursor aldehyde, [(see An Improved Process for Pioglitazone and Its Pharmaceutically Acceptable Salt; Lokeswara Rao Madivada et al., *Organic Process Research & Development* 2009 13(6), 1190-1194)], e.g., for rosiglitazone and pioglitazone as shown below.

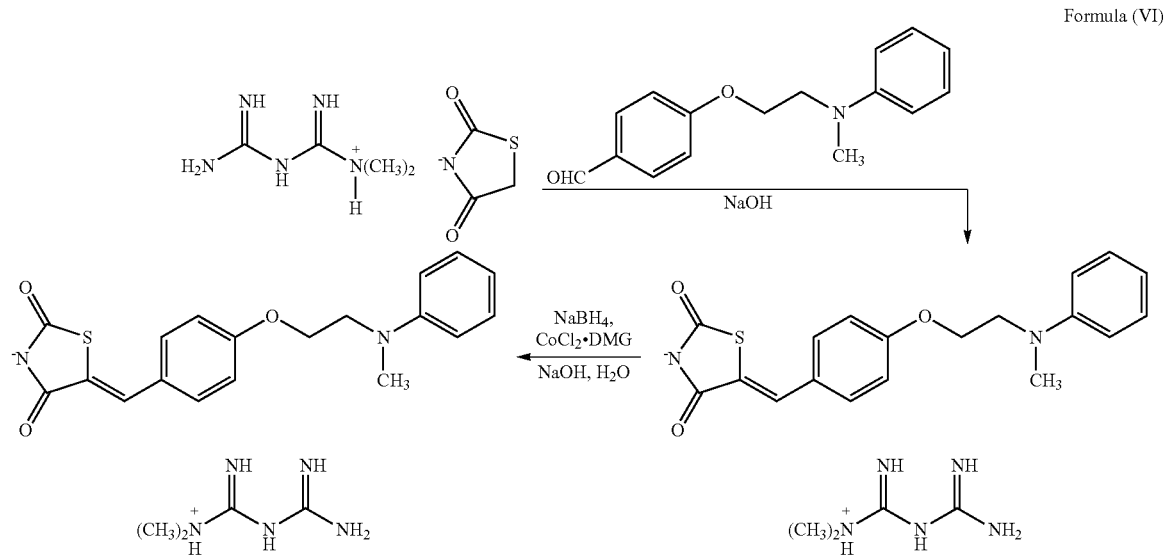

Formula (VI)

and

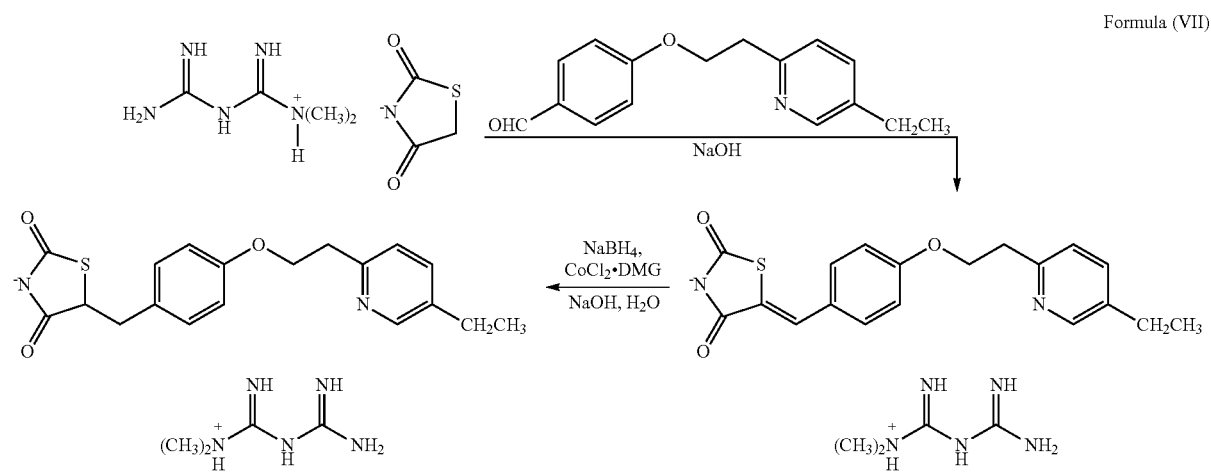

Formula (VII)

Alternatively, the pioglitazone or rosiglitazone metforminate salts were synthesized as follows:

Metformin. Pioglitazone salt of Formula (VII)

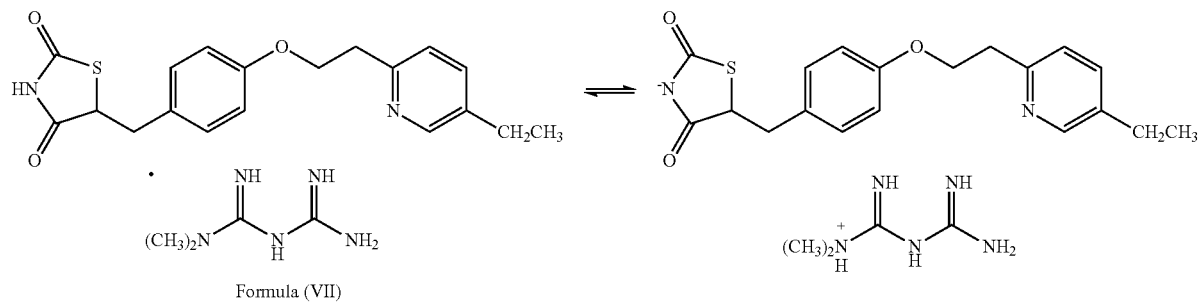

Formula (VII)

A mixture of metformin free base (100 mg, 0.774 mmol) and Pioglitazone (275 mg, 0.774 mmol, (from Combi-Blocks) were dissolved in hot deionized water (3 mL). The solution slowly cooled to RT. After filtration and drying, the procedure generated the mono metformin pioglitazone salt (240 mg, 64% yield) as a colorless solid, and is characterized by:

Melting Point: 179-181° C.

Chromatographic purity (HPLC): 100% (UV; area/area; λ=220 nm). Reference: NB#742-92

CHN analysis: Calculated for $C_{23}H_{31}N_7O_3S$: 56.89; C, 6.43; H, 20.19; N.

found: 56.92; C, 6.37; H, 20.20; N.

$^1$H NMR (300 MHz, DMSO-$d_6$): δ 8.34 (s, 1H), 7.56 (dd, 1H, J=9.0, 2.0 Hz), 7.26 (d, 1H, J=9.0 Hz), 7.17 (br s, 2H), 7.08 (d, 2H, J=8.1 Hz), 6.79 (d, 2H, J=8.1 Hz), 6.65 (br s, 4H), 4.27 (t, 2H, J=6.6 Hz), 4.12 (dd, 1H, J=10.2, 3.3 Hz), 3.29 (dd, 1H, J=13.8, 3.3 Hz), 3.11 (t, 2H, J=6.3 Hz), 2.91 (s, 6H), 2.66-2.50 (m, 4H), 1.16 (t, 3H, J=9.9 Hz).

$^{13}$C NMR (75 MHz, CDCl$_3$): δ 190.6, 181.8, 159.2, 158.2, 156.9, 155.5, 148.5, 136.8, 135.8, 132.0, 129.8, 123.1, 114.3, 66.8, 59.0, 39.3, 37.6, 37.0, 25.1, 15.6.

Single crystal x-ray structure of pioglitazone.metforminate, Formula (VII), was obtained as follows:

A clear colorless needle-like specimen of $C_{22}H_{30}H_8O_3S$, approximate dimensions 0.060 mm×0.265 mm×0.374 mm, was used for the X-ray crystallographic analysis. The X-ray intensity data were measured on a Bruker APEX-II CCD system.

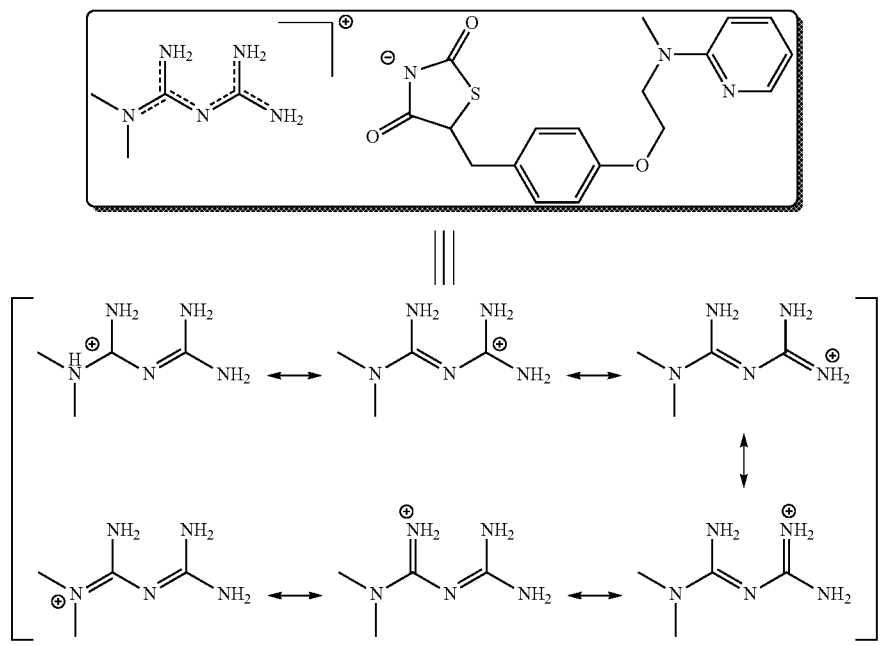

The integration of the data using an orthorhombic unit cell yielded a total of 53398 reflections to a maximum θ angle of 68.21° (0.83 Å resolution), of which 4335 were independent (average redundancy 12.318, completeness=98.4%, $R_{int}$=20.46%) and 2769 (63.88%) were greater than 2σ(F$^2$). The final cell constants of a=10.0068(6) Å, b=10.3890(7) Å, c=46.310(2) Å, volume=4814.4(5) Å$^3$, are based upon the refinement of the XYZ-centroids of 53 reflections above 20 σ(I) with 9.376°<2θ<49.09°. The ratio of minimum to maximum apparent transmission was 0.812. The calculated minimum and maximum transmission coefficients (based on crystal size) are 0.5970 and 0.9130.

The structure was solved and refined using the Bruker SHELXTL Software Package, using the space group P b c a, with Z=8 for the formula unit, $C_{22}H_{30}H_8O_3S$. The final anisotropic full-matrix least-squares refinement on $F^2$ with 356 variables converged at R1=6.78%, for the observed data and wR2=14.75% for all data. The goodness-of-fit was 1.076. The largest peak in the final difference electron density synthesis was 0.286 $e^-/Å^3$ and the largest hole was $-0.324$ $e^-/Å^3$ with an RMS deviation of 0.063 $e^-/Å^3$. On the basis of the final model, the calculated density was 1.343 $g/cm^3$ and F(000), 2064 $e^-$.

TABLE 1

Sample and crystal data for pioglitazone metforminate.

| | |
|---|---|
| Identification code | Pioglitazone.metforminate |
| Chemical formula | $C_{22}H_{30}N_8O_3S$ |
| Formula weight | 486.60 |
| Temperature | 100(2) K |
| Wavelength | 1.54178 Å |
| Crystal size | 0.060 × 0.265 × 0.374 mm |
| Crystal habit | clear colourless needles |
| Crystal system | orthorhombic |
| Space group | P b c a |
| Unit cell dimensions | a = 10.0068(6) Å   α = 90° |
| | b = 10.3890(7) Å   β = 90° |
| | c = 46.310(2) Å   γ = 90° |
| Volume | 4814.4(5) $Å^3$ |
| Z | 8 |
| Density (calculated) | 1.343 $g/cm^3$ |
| Absorption coefficient | 1.539 $mm^{-1}$ |
| F(000) | 2064 |

Figure 4:
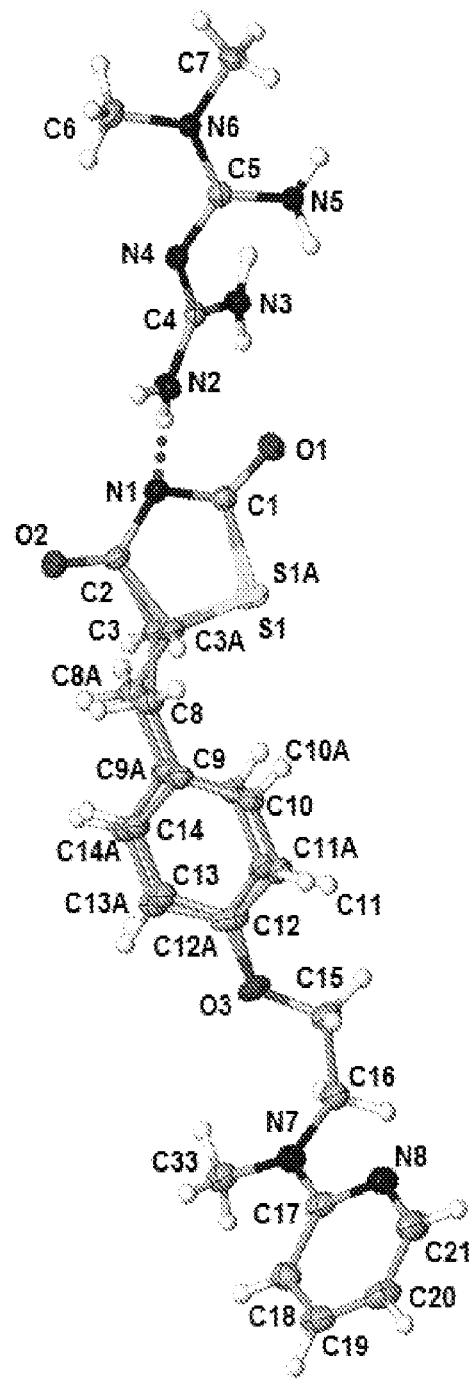

The molecular structure of pioglitazone metforminate showing the atom-labeling scheme, molecular disorder, and thiazolidine fragments is shown in FIG. 4. Displacement ellipsoids are drawn at the 50% probability level.

Figure 5:
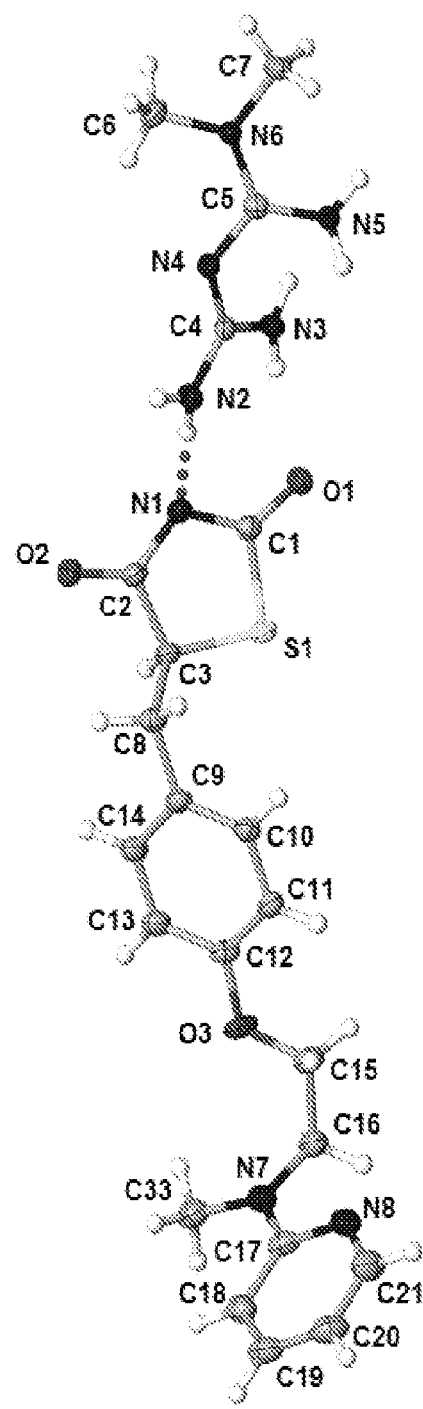

The molecular structure of pioglitazone metforminate, showing the atom-labeling scheme is shown in FIG. 5. Disorder components removed for clarity. Displacement ellipsoids are drawn at the 50% probability level.

Figure 6:
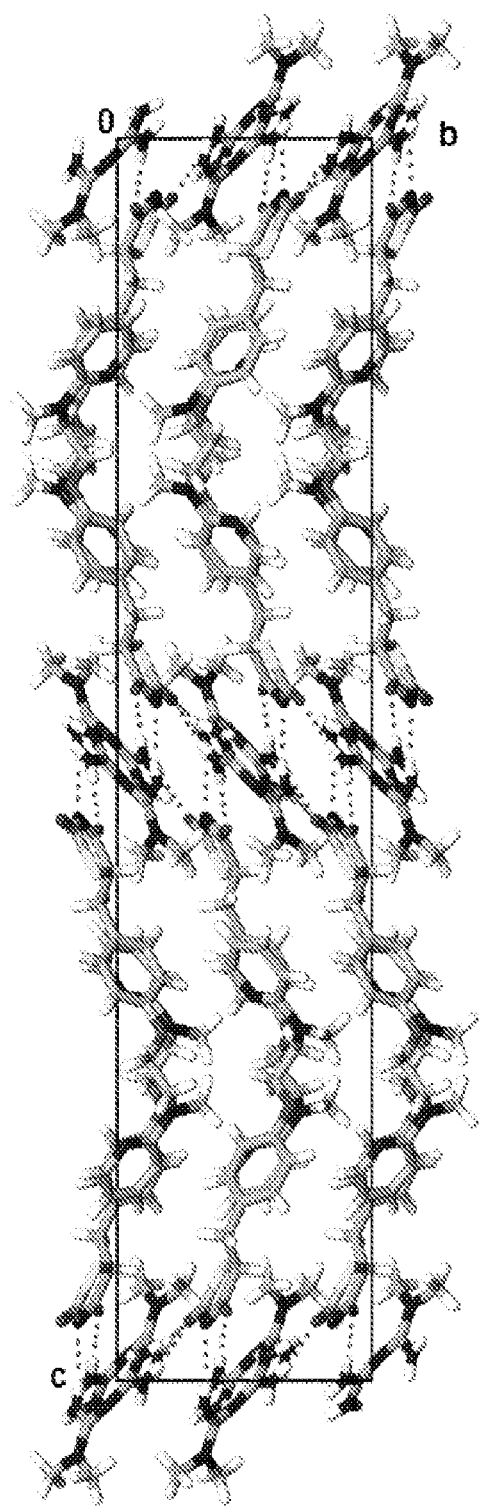

The crystal structure of pioglitazone.metforminate projected down the a-axis showing the extensive network of N—H . . . O/N hydrogen bonds is shown by FIG. 6.

Preparation of Rosiglitazone Metforminate (Formula VI)

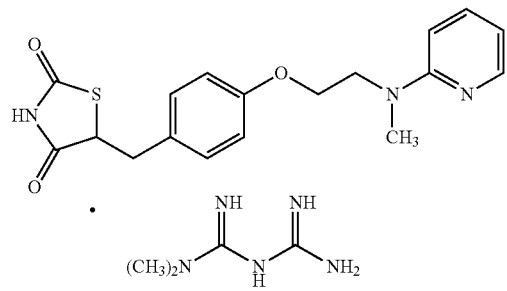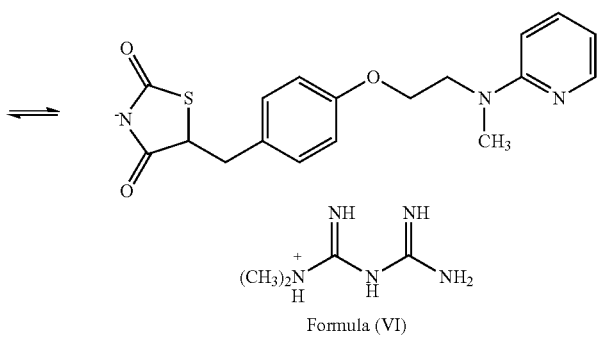

Formula (VI)

A mixture of metformin free base (36 mg, 0.279 mmol) and rosiglitazone (100 mg, 0.279 mmol, (98%, AK Scientific) were dissolved in 4 mL of hot water/ethanol solution (3.5 mL water, 0.5 mL ethanol). The solution slowly cooled to RT and stored in a −10° C. freezer overnight. After filtration and drying, the procedure generated the mono metformin rosiglitazone salt (88 mg, 65% yield) as a colorless solid, which is characterized by:

Melting Point: 184-186° C.;

Chromatographic purity (HPLC): 99.8% (UV; area/area; λ=220 nm). Reference: NB#742-95;

CHN analysis: Calculated for $C_{22}H_{30}N_8O_3S$: 54.30; C, 6.21; H, 23.03; N.

found: 54.40; C, 6.21; H, 23.18; N.

$^1$H NMR (300 MHz, DMSO-$d_6$): δ 8.06 (d, 1H, J=4.8 Hz), 7.49 (t, 1H, J=8.1 Hz), 7.17 (br s, 2H), 7.09 (d, 2H, J=8.1 Hz), 6.81 (d, 2H, J=8.1 Hz), 6.65-6.50 (m, 6H), 4.15-4.05 (m, 3H), 3.87 (t, 2H, J=5.4 Hz), 3.31 (d, 1H, J=13.8 Hz), 3.05 (s, 3H), 2.91 (s, 6H), 2.62 (dd, 1H, J=13.8, 10.5 Hz); and $^{13}$C NMR (75 MHz, CDCl$_3$): δ 190.7, 182.0, 159.3, 158.2, 158.1, 156.9, 147.6, 137.5, 132.1, 129.9, 114.2, 111.7, 105.9, 65.5, 59.1, 48.8, 39.4, 37.6, 37.3.

Biology: Anti-Hyperglycemic Activity of Met.TZ

The anti-diabetic activity of Met.TZ was examined in a standard mouse model of diabetes, in comparison to the front-line anti-diabetes drug metformin hydrochloride. Female db/db B6BKS (D) Leprdb/J mice of approximately 6.5 to 9.5 weeks old were used for this study. This is a standard genetic model of obesity related insulin resistance and diabetes, and has served as model animal for the development and analysis of many metabolically active drugs.

Two treatment groups of six female mice were administered Met.TZ (MetX), at dose levels of 44.7 mg/kg/dose or 149 mg/kg/dose. Two treatment groups of six female mice were administered the test sample TZ (X), at dose levels of 21.2 mg/kg/dose or 70.8 mg/kg/dose Two treatment groups of six female mice were administered the positive control article, metformin hydrochloride, at dose levels of 30 mg/kg/dose or 100 mg/kg/dose. One additional group of six mice served as the control and received the test article vehicle, water. All drugs and vehicle solutions were administered daily during the study via oral gavage at a dose volume of 5 mL/kg. Body weights were measured three times per week, at the time of glucose measurements.

Blood samples for glucose analysis were collected three times per week beginning on Day 1 through Day 26. Animals were fasted for 6 hours prior to glucose testing. On Days 1 through 12, the test article, positive control, and vehicle were administered after completion of the glucose testing. On Days 15 through 24 the dosing occurred approximately 90 minutes prior to glucose testing. On Day 26, a glucose tolerance test (GTT) was performed. The animals were administered a glucose solution at a dose level of 2 g/kg and a dose volume of 5 mL/kg. Blood collection for glucose measurements were collected predose, and at 0.5, 1, 1.5, 2, and 3 hours following administration of the glucose solution.

Results:

Body Weight Gain

Figure 7:
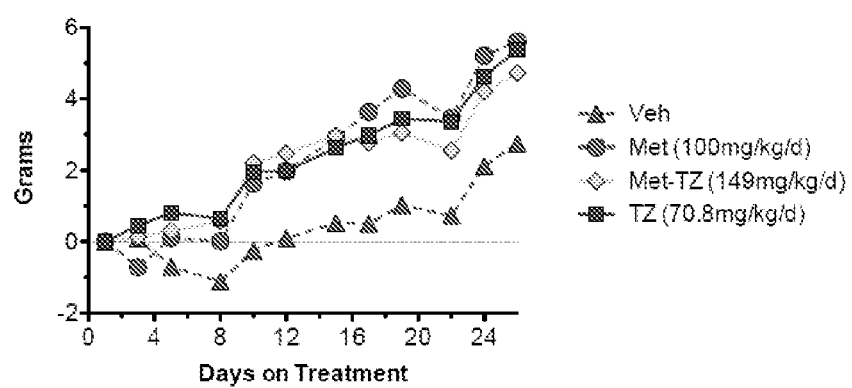
FIG. 7 shows a graphic presentation of increases in body weight in all treatment groups throughout the course of the study. The vertical axis shows the increase in weight in grams. The horizontal axis shows the days of treatment until the end of the study. The plotted symbols are: triangles are the vehicle alone; the circles are metformin alone at 100 mg/kg/day; the diamonds are the compound of Formula (I), Met-TZ, at 149 mg/kg/day; and the squares are 2,4-thiazolidinedione alone at 70.8 mg/kg/day.

All treatment groups showed increases in body weight throughout the course of the study. When differences in mean body weights at the start of the study were taken into account and the data were plotted as weight gain starting at day 1, it is clear that there were not significant differences in body weight gain between the treatment groups (see FIG. 7). Met.TZ Treatment was as Efficacious as Metformin in Reducing Fasting Glucose Levels:

Met.TZ treatment at 149 mg/kg (equivalent to a metformin dose of 100 mg/kg) showed striking glucose lowering activity from day 17 until the termination of the study. Met.TZ was more effective at lowering blood glucose than the equivalent dose of metformin, although this difference was not statistically significant.

TABLE 2

| | Fasting Blood Glucose (% changes from vehicle control) | | |
|---|---|---|---|
| Days of Treatment | Metformin (100 mg/kg/day) | Met.TZ (149 mg/kg/day) | TZ (70.8 mg/kg/day) |
| 15 | −9 | −13 | +34 |
| 17 | −34 | −51 | −22 |
| 19 | −7 | −33 | +9 |
| 22 | −43 | −52 | −19 |

Met.TZ was More Efficacious than Metformin in Reducing Glucose Intolerance

Figure 8:
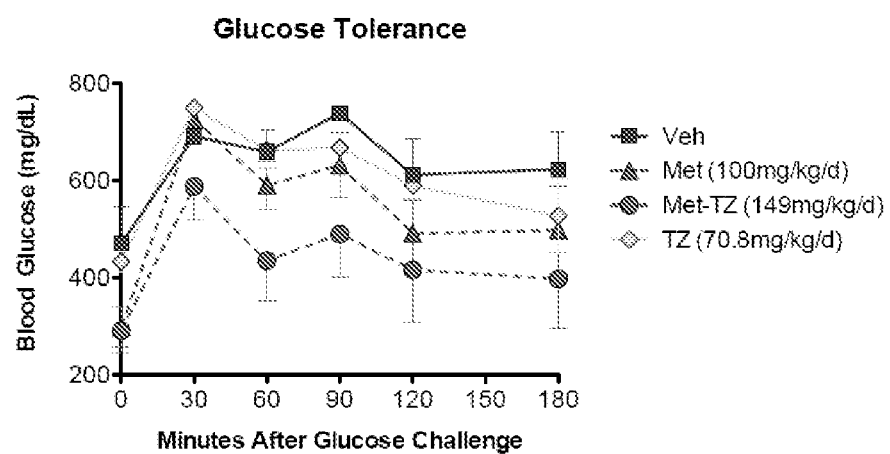
FIG. 8 shows a graphic presentation of the data of glucose tolerance on day 26 of the study, which clearly demonstrates that Met-TZ treatment resulted in striking improvement in glucose tolerance. At every time point post glucose administration, animals treated with 149 mg/kg/day of Met-TZ had lower glucose levels than animals treated with the equivalent dose of metformin. The vertical axis is the blood glucose in mg/dL; the horizontal axis is the minutes after glucose challenge. The plotted symbols are: squares are the vehicle alone; the triangles are metformin alone at 100 mg/kg/day; the circles are the compound of Formula (I), Met-TZ, at 149 mg/kg/day; and the diamonds are 2,4-thiazolidinedione alone at 70.8 mg/kg/day.

An oral glucose tolerance test performed on day 26 of the study demonstrated clearly that Met-TZ treatment resulted in striking improvement in glucose tolerance. At every time point post glucose administration, animals treated with 149 mg/kg/day Met.TZ had lower glucose levels than animals treated with the equivalent dose of metformin (see FIG. 8). Although the differences between the Met.TZ and metformin curves were not statistically significant, the Met.TZ curve, but not the metformin curve, was significantly different than that from control animals (Veh); * P<0.05 by ANOVA. Data are plotted as means of 6 animals, +/−SEM.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A compound of Formula (A) comprising:

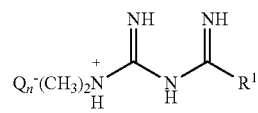

Formula (A)

wherein:
when n is 1, then $R^1$ is —$NH_2$;
and Q is

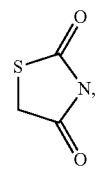

and
with the proviso that a neutral compound of Formula (A) is obtained.

2. The compound of Formula (A) of Claim 1 wherein the ompound is ≥95% chemically pure.

3. A pharmaceutical formulation having as its active ingredient a compound of Formula (A) of claim 1 with one or more pharmaceutically-acceptable adjuvants, hinders, desiccants, diluents, excipients, buffers, and preservatives.

4. The pharmaceutical formulation of claim 3 having as its active ingredients: rosiglitazone metformin salt as shown be the formula Formula (VI); in combination with a composition of Formula (A) of metformin and thiazolidinedione in a ratio of 1:1 as shown by the formula Formula (I); wherein 2 mg of Formula (VI) are combined with 500 mg of Formula (I).

5. The pharmaceutical formulation of claim 3 having as its active ingredients: pioglitazone metformin salt as shown be the formula Formula (VII); in combination with a composition of Formula (A) of metformin and thiazolidinedione in a ratio of 1:1 as shown by the formula Formula (I); wherein 15 mg of Formula (VI) are combined with 500 mg of Formula (I).

6. The pharmaceutical formulation of claim 3 in the form of a tablet, capsule, oral use syrup, suspension, emulsion, solution for injection, or sustained release long acting formulations.

7. A method for treating a patient having cardiovascular diseases, type2: diabetes, gestational diabetes, polycystic ovary syndrome, non-alcoholic fatty liver disease, premature puberty comprising administrating to the patient a pharmaceutical formulation of claim 3 once or twice per day.

* * * * *